United States Patent [19]

Kato et al.

[11] Patent Number: 5,452,614
[45] Date of Patent: * Sep. 26, 1995

[54] DYNAMIC VISCOELASTICITY APPARATUS

[75] Inventors: Hidetaka Kato; Nobutaka Nakamura, both of Tokyo, Japan

[73] Assignee: Seiko Instruments Inc., Tokyo, Japan

[*] Notice: The portion of the term of this patent subsequent to Feb. 22, 2011 has been disclaimed.

[21] Appl. No.: 135,483

[22] Filed: Oct. 13, 1993

[30] Foreign Application Priority Data

Oct. 13, 1992 [JP] Japan ................................. 4-274556

[51] Int. Cl.$^6$ ................................................. G01D 3/00
[52] U.S. Cl. ..................... 73/789; 73/808; 73/856
[58] Field of Search ..................... 73/789, 808, 812, 73/817, 826, 852, 806

[56] References Cited

U.S. PATENT DOCUMENTS

| | | | |
|---|---|---|---|
| 4,266,424 | 5/1981 | Muenstedt | 73/789 |
| 4,283,955 | 8/1981 | Nagy et al. | 73/789 X |
| 4,297,884 | 11/1981 | Lêvêque et al. | 73/789 X |
| 4,352,292 | 10/1982 | Madigosky et al. | 73/574 X |
| 4,794,788 | 1/1989 | Masters et al. | 73/54.27 |
| 4,794,798 | 1/1989 | Matsushita et al. | 73/789 |
| 4,967,601 | 11/1990 | Teramoto | 73/789 |
| 5,046,367 | 9/1991 | Iizuka | 73/789 |
| 5,079,956 | 1/1992 | Burhin et al. | 73/846 |
| 5,277,200 | 1/1994 | Kawazoe et al. | 73/575 X |
| 5,287,749 | 2/1994 | Nakamura | 73/808 |

*Primary Examiner*—Richard E. Chilcot, Jr.
*Assistant Examiner*—Max H. Noori
*Attorney, Agent, or Firm*—Spensley Horn Jubas & Lubitz

[57] ABSTRACT

Phase delay, amplitude and the like of sinusoidal strain (stress) are detected with high precision, and also adverse influences caused by expansion, shrinkage, stress relaxation, and creep of a sample are removed by a simple correction term by way of a mathematical method, utilizing Fourier transformation processing. A digital-to-analog converter is used for converting a signal of a detector for detecting sample strain, or displacement of the sample, a memory is connected for storing a digital output signal from the analog-to-digital converter, and a calculator is used for performing a Fourier transformation calculation on the signal values stored in the memory. Complex elastic modulus M* and loss tangent tan δ corresponding to the basic physical amount in dynamic viscoelasticity can be obtained with high precision by processing a response signal derived from the sample by Fourier transformation processing. Also, the measuring range of the elastic modulus can be expanded.

2 Claims, 3 Drawing Sheets

DYNAMIC VISCOELASTICITY APPARATUS

BACKGROUND OF THE INVENTION

The present invention relates to a dynamic viscoelasticity measuring apparatus.

Conventionally, in such apparatus both an amplitude "Xo" and a phase delay time "τ" of sinusoidal strain with respect to sinusoidal stress are measured. The amplitude and phase delay time are needed to calculate basic physical quantities for a viscoelasticity measurement, i.e. loss tangent tan δ, loss elastic modulus E", and storage elastic modulus E'. T and Xo can be measured in accordance with the following methods, which will be described with reference to FIG. 3:

1) T-measuring method: There are provided a force generator for applying a stress having a sinusoidal variation with time to a sample and a zero-crossing detector in a strain detector for detecting a corresponding sinusoidally varying strain of the sample. It is assumed that time measured after a zero crossing point of a sinusoidal stress waveform, or signal, has been detected and until a zero crossing point of sinusoidal strain is detected, is equal to τ.

2) Xo-measuring method: There is employed a maximum value, or upper-side peak, detecting circuit for a sinusoidal strain waveform, or signal, and a minimum value, or lower-side peak, detecting circuit for this sinusoidal strain waveform. Half the difference between the upper-side peak "Xa" of the strain waveform and the lower-side peak "Xb" is regarded as an amplitude Xo of the sinusoidal strain waveform.

In the above-described conventional measuring methods, if high-frequency noise is present in the sinusoidal strain waveform, then the sinusoidal strain waveform could have a zero point crossing earlier than would a noise-free sinusoidal strain waveform due to the high-frequency noise in the phase difference detection. In the case of amplitude detection, high-frequency noise is likely to result in detection of a higher maximum amplitude value and/or a lower minimum amplitude value of the sinusoidal strain waveform than would be detected if such noise were not present in the strain waveform. It will be noted that the only parts of the strain waveform signal used to obtain measurement data are the zero crossing points and the maximum and minimum peaks of the strain waveform and as long as the stress signal is sinusoidal a noise-free strain signal will be at least substantially sinusoidal.

The above-described errors caused by noise may be eliminated or mitigated by employing a means for Fourier-transforming the strain waveform to derive a strain waveform having the same frequency as the stress waveform. As a consequence, precision of measurement data may be improved, errors due to noise may be lowered, and the useful measurement range for elastic modulus may be expanded.

SUMMARY OF THE INVENTION

The present invention provides a solution to the above-described problem and is embodied in the following apparatus. Specifically, dynamic viscoelasticity measuring apparatus according to the present invention is mainly comprised of a function generator for generating a sinusoidal signal having a desirable frequency; a stress applicator connected to the function generator, for applying sinusoidal stress having the waveform of the sinusoidal signal to a sample; a strain detector for detecting sinusoidal strain produced in the sample in response to the sinusoidal stress; an analog-to-digital converter for A/D-converting the sinusoidal stress applied to the sample and the strain detected by the detector; a memory device for storing outputs derived from the analog-to-digital converter; and a calculator for performing a Fourier transformation on data stored in the memory device. In this dynamic viscoelasticity measuring apparatus, the sinusoidal strain is Fourier-transformed to derive a strain signal "ωy" and a signal having the same frequency component as that of the sinusoidal stress, so that adverse influence caused by a drift in the strain signal due to a noise component and/or creep of the sample can be eliminated.

The dynamic viscoelasticity measuring apparatus with the above-described construction has the following effects. First, the sine wave corresponding to the output of the function generator is converted into a sinusoidal stress by the stress applicator, which stress will then be applied to the sample. The stress induces strain in the sample in accordance with viscoelasticity characteristics of the sample. Strain of the sample is detected by the strain detector. After both the stress signal from the stress applicator and the output of the strain detector have been A/D-converted into corresponding digital data, these digital data are stored in the memory device in a predetermined form. The digital data stored in the memory device are read out by the calculator. Then, the calculator performs a calculation based upon the following formula to output a dynamic viscoelasticity measurement value of the sample.

$$\oint : \text{Integral on the closed curve}$$
$$a = \oint F(\omega t) \cos(\omega t)\, d(\omega t)$$
$$b = \oint F(\omega t) \sin(\omega t)\, d(\omega t)$$
$$A = \oint x(\omega t) \cos(\omega t)\, d(\omega t)$$
$$B = \oint x(\omega t) \sin(\omega t)\, d(\omega t)$$

$$M^*(\omega) = \frac{Aa + Bb + i(Ab - Ba)}{\alpha(A^2 + B^2)}$$

where symbols are defined as follows:
F: force (stress) exerted by the stress generator,
x: strain detected by the strain detector,
ω: sine wave frequency,
t: time,
$M^*(\omega)$: complex elastic modulus of the sample with respect to the frequency ω,
α: a constant which is specific to, and dependent on, the sample, and $$i: \sqrt{-1}\,.$$

In a tension type viscoelasticity measuring apparatus, when expansion, shrinkage, creep and the like occur in a sample, a strain waveform is measured as illustrated in FIG. 4. Only a first order term is eliminated from parameters of this waveform by a correction term.

That is, assuming now that:

$$x(\omega t) = x_r(\omega t) + \frac{\Delta x}{T} t$$

$$x_r(\omega t) = A_1 \cos\omega t + B_1 \sin\omega t$$

then based on:

$$A = \oint x(\omega t) \cos(\omega t) \, d(\omega t) = A_1$$
$$B = \oint x(\omega t) \sin(\omega t) \, d(\omega t) = B_1 - \frac{\Delta x}{\pi},$$

$$M^*(\omega) = \frac{A_1 a + B_1 b + i(A_1 b - B_1 a)}{\alpha(A_1^2 + B_1^2)}$$

where symbols are defined as follows:

$\Delta x$: a drift amount for one period of a sinusoidal signal, and

T: one period of the strain wave, i.e. T= $2\pi/\omega$ $X_r(\omega t)$: a true strain waveform containing no low frequency/high frequency components.

DESCRIPTION OF THE PREFERRED EMBODIMENTS

Referring now to drawings, the present invention will be described more in detail.

Figure 1:
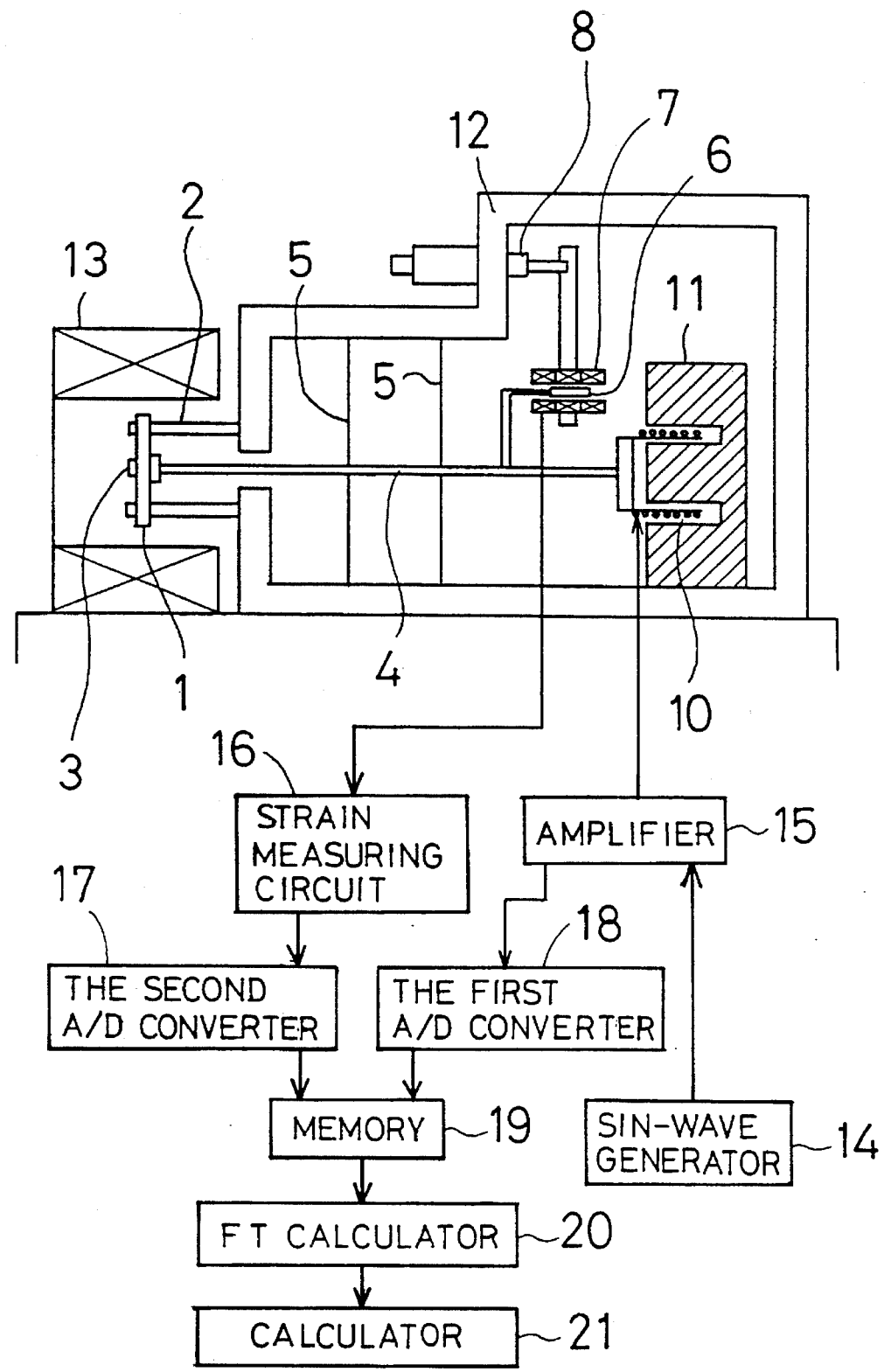
FIG. 1 is partly a pictorial view and partly a block diagram showing a preferred embodiment of the present invention.

In FIG. 1 there is shown a first preferred embodiment of the present invention in which a sample 1 is held or fixed via two opposed ends in a sample chuck 3. The chuck 3 is fixed to a probe 4. Movement of the probe 4 is defined along a straight line (one-dimensional) direction, horizontal and parallel to the plane of FIG. 1, since the probe 4 is elastically fixed to a housing 12 by two leaf springs 5. A core 6 is fixed to a portion of the probe 4, and displacement of the core 6, and probe 4, is detected with the aid of a strain detecting differential transformer 7 arranged around the core 6. Positioning of the differential transformer 7 is determined by a micrometer 8 attached to the housing 12. A coil 10 is fixed to one end of the probe 4, and a magnet 11 fixed on the housing 12 is arranged in such a manner that the coil 10 is coupled with this magnet 11. Coil 10 and magnet 11 together constitute a force generator.

On the other hand, a furnace 13 is arranged around the sample 1 for the purpose of setting a temperature environment for the sample 1. In FIG. 1, reference numeral 14 indicates a sine wave generator. An output (since wave signal) of the sine wave generator 14 is controlled with respect to its amplitude by an amplifier 15. The amplitude-controlled sine wave signal is supplied to the coil 10, so that a sinusoidal force is produced in conjunction with the magnet 11. A displacement detection signal produced by the differential transformer 7 and the core 6 is supplied to a displacement detecting, or strain measuring, circuit 16 which then generates a displacement signal.

Furthermore, the output of the amplifier 15 is converted into a digital output value by a first A/D converter 18 having such features as 12-bit resolution and high-speed operation. Then, the digital output value is furnished to a memory 19.

On the other hand, the output of the displacement detecting circuit 16 is A/D converted into a digital output value by a second A/D converter 17 having such features as 12-bit resolution and high-speed operation, and then the resultant digital output value is stored into the memory 19.

Operation of the dynamic viscoelasticity measuring apparatus according to this preferred embodiment will now be described. First, a sine wave signal having a desired frequency, f, is produced by the sine wave generator 14. After the amplitude of this sine wave signal is properly controlled or adjusted by the amplifier 15, the amplitude-controlled sine wave is transferred to the coil 10 which produces a sinusoidal force in conjunction with the magnet 11. The generated sinusoidal force is applied as a bending (deflection) stress to the sample 1 through the probe 4 and the chuck 3. On the other hand, at this time, bending (deflection) strain occurring at the sample 1 is transferred to the core 6 through the chuck 3 and the probe 4, and is detectable as displacement of the core 6 with respect to the differential transformer 7.

Under a condition of measuring a dynamic viscoelasticity characteristic, both of the first A/D converter 18 and the second A/D converter 17 commence the A/D converting operations every 10 microseconds. The digital signals derived from the first and second A/D converters 18 and 17 are stored into the memory 19 every 1/1000f seconds with respect to the output frequency f(Hz) of the sine wave generator 14. As a result, data about 1 period (T=1/f) are stored into the memory every time 1000 sets of digital signals, representing 1000 strain-stress curve coordinate values, have been acquired. During this operation, the temperatures of the furnace 13 are controlled in accordance with the traditional controlling method, so that the temperature of the sample 1 is set to an arbitrary temperature.

It is assumed that the data stored in the memory 19 are Fi, xi (i=1, 2, . . . ). When the data acquired for 4 periods, namely i=4000, have been stored in the memory, 8000 pieces of data Fi, xi (i=1 to 4000) are transferred to the Fourier-Transformation calculator 20 by which the below-mentioned calculation will be carried out. After the data have been sent to the Fourier-Transformation calculator 20 from the memory 19, the data stored in this memory 19 are cleared, and new data (i=1 to 4000) which are being continuously transferred from the first and second A/D converters 18 and 17, are again stored in the memory.

$$a = \frac{2}{1000} \sum_{i=2001}^{3000} Fi \cos\left(\frac{2\pi i}{1000}\right)$$

$$b = \frac{2}{1000} \sum_{i=2001}^{3000} Fi \sin\left(\frac{2\pi i}{1000}\right)$$

$$A = \frac{2}{1000} \sum_{i=2001}^{3000} xi \cos\left(\frac{2\pi i}{1000}\right)$$

$$B = \frac{2}{1000} \sum_{i=2001}^{3000} xi \sin\left(\frac{2\pi i}{1000}\right)$$

It should be noted that the data acquired during the first 2 periods (i=1 . . . 2000) among the 4 periods are discarded because of transient responses occurring at the beginning of data measurement. The values "a", "b", "A" and "B" which have been calculated in the Fourier-Transformation calculator 20 are sent to the calculator 21 by which the below-mentioned calculations are carried out to obtain the complex loss elastic modulus and the loss tangent:

$$M^* = \frac{Aa + Bb + i(Ab - Ba)}{\alpha(A^2 + B^2)}$$

$$\tan\delta = \frac{A}{B}$$

It should also be noted that the temperatures of the furnace 13 is controlled by a conventional temperature controlling method, whereby the temperature of the sample 1 may be arbitrarily set.

Figure 2:
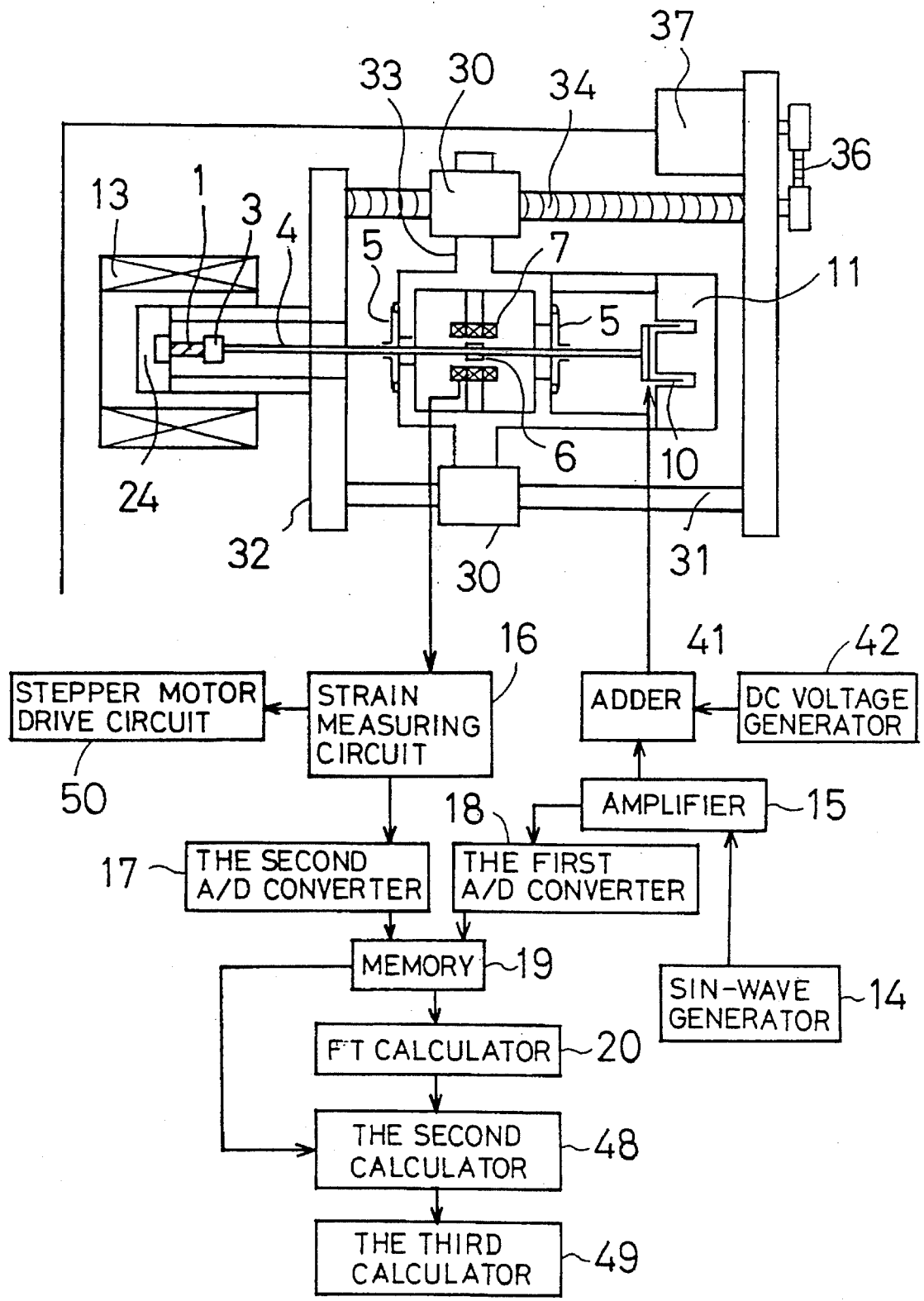
FIG. 2 is a view similar to that of FIG. 1 showing another preferred embodiment of the present invention.
Figure 3:
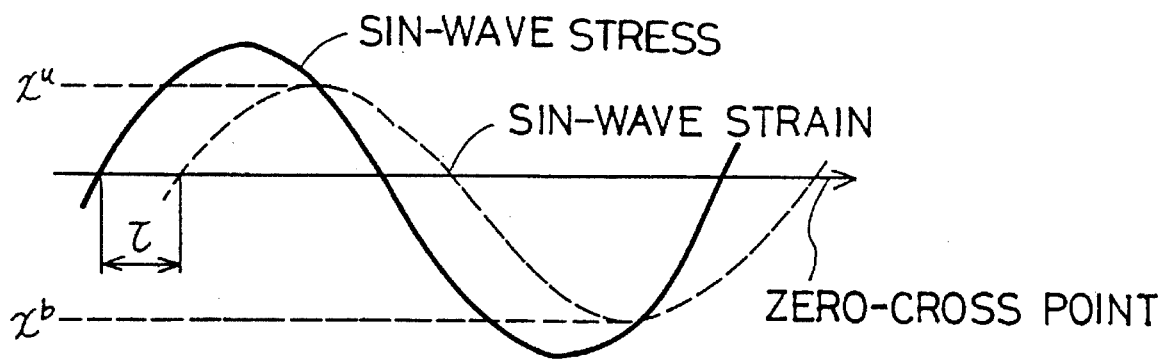
FIG. 3 is a waveform diagram illustrating the conventional method for detecting the amplitude and the phase delay of a strain waveform.
Figure 4:
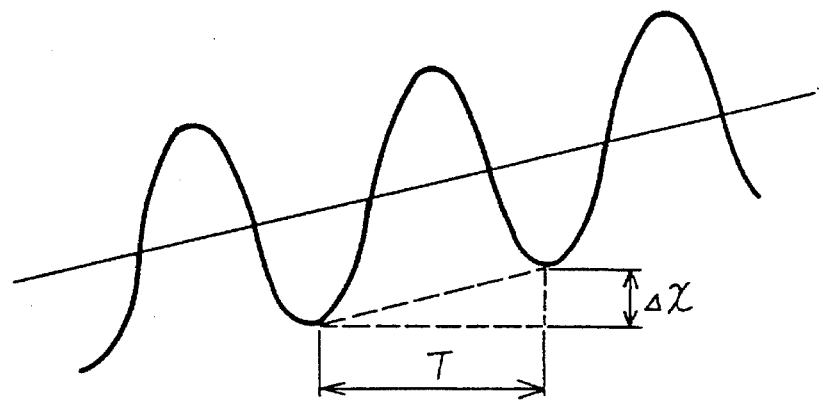
FIG. 4 is a waveform diagram showing a strain waveform when a sample is under expansion, shrinkage, or creep conditions.

FIG. 2 represents another dynamic viscoelasticity measuring apparatus according to a second preferred embodiment of the present invention. In FIG. 2, one end of sample 1 is held by a holder 24 coupled to a housing base 32, and a sample chuck 3 is coupled to one end of a probe 4. The probe 4 is elastically fixed to a mechanism portion holding member 33 by way of two leaf springs 5. The movement of the probe 4 is confined to a linear movement in the direction of the axis of probe 4, which may coincide with the axis of sample 1. To one end of the probe 4, a core 6 for a differential transformer used to detect displacement is fixed. The differential transformer 7 is held around the core 6 in such a manner that this differential transformer 7 is fixed to the above-explained mechanism holding member 33, which constitutes a strain detector for detecting relative displacement of the core 6, corresponding to strain experienced by sample 1. A coil 10 is fixed to the other end of probe 4, whereas a magnet 11 fixed to the above-described mechanism portion holding member 33 is arranged in such a manner that the coil 10 is coupled to magnet 11. Magnet 11 and the coil 10 together constitute an electromagnetic force generator.

On the other hand, furnace 13 for arbitrarily setting the temperatures of the sample is arranged around sample 1. After the amplitude of a sinusoidal voltage signal corresponding to an output from a sine wave generator 14 is controlled by an amplifier 15, the amplitude-controlled sinusoidal voltage signal is sent to an adder 41 by which this sinusoidal voltage signal is added to an output of a DC voltage generator 42. An output derived from the adder 41 causes a sinusoidal force with a DC bias to be produced between the coil 10 and the magnet 11, while being supplied to the coil 10. The produced force further causes strain in the sample 1 via the probe 4 and the sample chuck 3. The strain occurring in the sample 1 is transferred via the probe 4 to the core 6 as the above-described core movement. This strain is detected by the differential transformer 7, and a strain signal detected by the differential transformer 7 is supplied to a displacement detecting, or strain measuring, circuit 16.

On the other hand, the mechanism portion holding member 33 is engaged via bearings 30 to a ball screw 34 and a guide rod 31, and is moved along the axial direction of the ball screw 34 in response to rotation of the ball screw 34 driven by a drive belt 36 which is advanced by an increment type stepper motor 37. In other words, the above-described guide rod 31, the ball screw 34, the bearings 30, the stepper motor 37, and the drive belt 36 wholly constitute a transportation mechanism for the mechanism portion holding member 33. The stepper motor 37 is driven in response to an output signal of a stepper motor drive circuit 50. This output signal from the stepper motor drive circuit 50 is determined based upon the output from the displacement detecting circuit 16.

Furthermore, the output signal from the amplifier 15 is A/D-converted into a corresponding digital value by a first A/D converter 18 having 12-bit resolution and high-speed operation. The resultant digital value is supplied to and stored in memory 19. Also, the output signal from the displacement detecting circuit 16 is A/D-converted into a corresponding digital value by a second A/D converter 17 having 12-bit resolution and high-speed operation. The A/D-converted displacement signal is supplied to and stored in the memory 19.

A description will now be made of an operation of the dynamic viscoelasticity measuring apparatus according to this second preferred embodiment. When a DC force is produced between the coil 10 and the magnet 11 in response to the DC voltage signal generated by DC voltage generator 42, and a tension change occurs in sample 1 due to thermal expansion, softening, and other reasons, strain having a finite, non-zero value is created and is measured by the displacement detecting circuit 16. Then stepper motor 37 is controlled by stepper motor drive circuit 50 in order to zero the strain signal from circuit 16. When the strain output of the displacement detecting circuit 16 enters a preselected range (for instance, ±1 µm, the sine wave generator 14 commences its generating operation, i.e., the present state is transferred to a so-called state for measuring dynamic viscoelasticity. At this time, the sine wave generator 38 is so arranged as to output sine wave signals at the respective frequencies of 0.01 Hz, 0.02 Hz, 0.05 Hz, 0.1 Hz, 0.2 Hz, 0.5 Hz, 1 Hz, 5 Hz, 10 Hz, 20 Hz, 50 Hz, and 100 Hz.

Under a condition of measuring a dynamic viscoelasticity characteristic, both of the first A/D converter 18 and the second A/D converter 17 commence the A/D converting operations every 10 microseconds. The digital signals derived from the first and second A/D converters 18 and 17 are stored into the memory 19 every 1/1000f seconds with respect to the output frequency f(Hz) of the sine wave generator 14. As a result, data acquisition about 1 period (T=1/f) is completed every time 1000 sets of data points, i.e. 1000 sets of stress and associated strain values, have been acquired. It is assumed that the data stored in the memory 19 are Fi, xi (i=1, 2 ... ). When the data acquired for 4 periods, namely i=4000 have been stored in the memory 19, 8000 pieces of data Fi, xi (i=1 to 4000) are transferred to the Fourier-Transformation calculator 20 by which the below-mentioned calculation will be carried out. After the data have been set to the Fourier-Transformation calculator 20 from the memory 19, the data stored in this memory 19 are cleared, and the data (i=1 to 4000) which are continuously transferred from the first and second A/D converters 18 and 17, are again stored in the memory.

$$a = \frac{2}{1000} \sum_{i=2001}^{3000} Fi \cos\left(\frac{2\pi i}{1000}\right)$$

$$b = \frac{2}{1000} \sum_{i=2001}^{3000} Fi \sin\left(\frac{2\pi i}{1000}\right)$$

$$A = \frac{2}{1000} \sum_{i=2001}^{3000} xi \cos\left(\frac{2\pi i}{1000}\right)$$

$$B = \frac{2}{1000} \sum_{i=2001}^{3000} xi \sin\left(\frac{2\pi i}{1000}\right)$$

It should be noted that the data acquired during the first 2 periods (i=1 to 2000) among the 4 periods are discarded because of a transient response occurring at the beginning of data measurement The values "a" "b" "A" and "B" which have been calculated by the Fourier-Transformation calculator 20 are sent to the second calculator 48 by which the below-mentioned calculations are carried out so as to correct for expansion, shrinkage, and creep:

$$\Delta x = x(3000) - x(2001) \quad B_1 = B + \Delta X/\tau$$

Subsequently, both of the values of "a", "b" and "A" which have been calculated by the Fourier-Transformation calculation 20, and the value of "$B_1$" which has been calculated by the second calculator 48 are supplied to a third calculator 49 by which the following calculation is performed to obtain complex elastic modulus and loss elastic modulus.

$$M^* = \frac{Aa + B_1 b + i(Ab - B_1 a)}{\alpha(A^2 + B_1^2)}$$

$$\tan \delta = \frac{A}{B_1}$$

When the measurement for a predetermined frequency has been completed, the dynamic viscoelasticity measurement is interrupted. After the stepper motor 37 is again controlled in accordance with the above-described method, a subsequent measurement at a different frequency is commenced. Then, this measuring cycle is repeated. During this measuring cycle, the temperatures of the furnace 13 are controlled in accordance with a conventional method, so that the temperature of the sample 1 is set to an arbitrary temperature.

As previously described in detail, in accordance with the present invention, since all of the data about stress (Fi) and strain (xi) are effectively utilized, the precision of the viscoelasticity measurement can be improved. Also, since the terms caused by expansion, shrinkage, and creep can be removed by the calculation process, there are the advantages that the measurement value of the dynamic viscoelasticity can be readily obtained, and performance of the dynamic viscoelasticity analyzing apparatus can be improved.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A dynamic viscoelasticity apparatus comprising:

means for holding a sample;

means for applying a sine wave strain deformation through said means for holding the sample and for providing a signal representative of the sine wave strain deformation;

detector means for producing a signal representative of a response by the sample to the strain deformation applied by said applying means;

means for varying the temperature of the sample;

first analog-to-digital converter means for converting the signal produced by said detector means into a corresponding digital deformation signal;

second analog-to-digital converter means for converting the signal produced by said means for applying a sine wave strain deformation into a corresponding digital strain signal;

memory means for storing the digital deformation and strain signals from said first and second analog-to-digital converter means within predetermined periods of the sine wave strain deformation;

calculator means for performing Fourier transformation calculation using digital deformation and strain signals in said memory means and for calculating the result of the Fourier transformation calculation to correct for creep based on the change in the signal produced by said detector means during one period of the sine wave and for performing calculations of sample dynamic viscoelasticity based on the result of the Fourier transformation calculation; and memory clear means for clearing the digital signals stored in said memory means just after transferring the signals of the memory means to the calculator means so as to prepare said memory means for storing new signals from the first and second analog-to-digital converter means.

2. Apparatus as defined in claim 1, wherein said calculator means comprise:

a Fourier transformation calculator for performing calculation in form of $$B = \int x(\omega t) \sin(\omega t) \, d(\omega t)$$

where: x is strain in the sample; $\omega$ is the frequency of variation of the strain deformation; and a further calculator for performing such a calculations such as $B_1 = B + \Delta x/\tau$ with respect to the calculation result B which is calculated by said Fourier transformation calculator, where $\Delta x$ is the change in the signal produced by said detector means during one period of variation of the strain deformation.

* * * * *